(12) United States Patent
Sakanishi et al.

(10) Patent No.: US 9,464,036 B2
(45) Date of Patent: Oct. 11, 2016

(54) THICKENING STABILIZER, AND THICKENING/STABILIZING COMPOSITION USING THE SAME

(71) Applicants: DAICEL CORPORATION, Osaka-shi, Osaka (JP); YAMAGUCHI UNIVERSITY, Yamaguchi-shi, Yamaguchi (JP)

(72) Inventors: Yuichi Sakanishi, Ohtake (JP); Takashi Saeki, Ube (JP); Yusuke Narusaka, Ube (JP); Mami Itoh, Ube (JP)

(73) Assignees: DAICEL CORPORATION, Osaka-shi (JP); YAMAGUCHI UNIVERSITY, Yamaguchi-shi (JP)

( * ) Notice: Subject to any disclaimer, the term of this patent is extended or adjusted under 35 U.S.C. 154(b) by 0 days.

(21) Appl. No.: 14/761,817

(22) PCT Filed: Feb. 4, 2014

(86) PCT No.: PCT/JP2014/052534
§ 371 (c)(1),
(2) Date: Jul. 17, 2015

(87) PCT Pub. No.: WO2014/123110
PCT Pub. Date: Aug. 14, 2014

(65) Prior Publication Data
US 2015/0376119 A1    Dec. 31, 2015

(30) Foreign Application Priority Data

Feb. 8, 2013 (JP) ................. 2013-022906

(51) Int. Cl.
| | |
|---|---|
| A23L 1/05 | (2006.01) |
| A61K 47/18 | (2006.01) |
| A61K 47/44 | (2006.01) |
| A61K 8/42 | (2006.01) |
| A61K 9/06 | (2006.01) |
| A61Q 19/00 | (2006.01) |
| C07C 235/84 | (2006.01) |
| C09D 7/00 | (2006.01) |
| C09K 3/00 | (2006.01) |
| C08K 5/20 | (2006.01) |

(52) U.S. Cl.
CPC ............ *C07C 235/84* (2013.01); *A23L 1/05* (2013.01); *A61K 8/42* (2013.01); *A61K 9/06* (2013.01); *A61K 47/44* (2013.01); *A61Q 19/00* (2013.01); *C09D 7/002* (2013.01); *C09K 3/00* (2013.01); *A23V 2002/00* (2013.01); *A61K 47/18* (2013.01); *A61K 2800/10* (2013.01); *A61K 2800/48* (2013.01); *C08K 5/20* (2013.01)

(58) Field of Classification Search
CPC ........ A23L 1/05; A61K 47/18; A61K 47/44; A61K 8/42; A61K 9/06; A61K 2800/10; A61K 2800/48; A61Q 19/00; C07C 235/84; C09D 7/002; C09K 3/00; A23V 2002/00; C08K 5/20

See application file for complete search history.

(56) References Cited

U.S. PATENT DOCUMENTS

| | | |
|---|---|---|
| 6,284,924 B1 | 9/2001 | Ueno et al. |
| 2004/0010056 A1 | 1/2004 | Takahashi et al. |
| 2013/0085087 A1 | 4/2013 | Mesher et al. |

FOREIGN PATENT DOCUMENTS

| | | |
|---|---|---|
| CN | 102775325 A | 11/2012 |
| EP | 1 095 930 A1 | 5/2001 |
| EP | 1 375 611 A2 | 1/2004 |
| JP | 1-163111 A | 6/1989 |
| JP | 2004-217884 A | 8/2004 |
| JP | 2006-257382 A | 9/2006 |
| JP | 2008-251581 A | 10/2008 |
| WO | WO 00/68178 A1 | 11/2000 |
| WO | WO 2012/168151 A1 | 12/2012 |
| WO | WO 2013/040718 A1 | 3/2013 |

OTHER PUBLICATIONS

Sagara et al., "Material Design for Piezochromic Luminescence: Hydrogen-Bond-Directed Assemblies of a Pyrene Derivative," J. Am. Chem. Soc., 129, 1520-1521, 2007.*
Chen et al., "A Fluorescence Sensor for Detection of Geranyl Pyrophosphate by the Chemo-Ensemble Method", Journal of Organic Chemistry, vol. 74, No. 2, 2009, pp. 895-898.
Inoue et al., "Gelator and Thickener Derived from Dimethyl 5-Aminoisophthalate", Chemistry Letters, vol. 34, No. 3, 2005, pp. 348-349.

(Continued)

*Primary Examiner* — Paul A Zucker
*Assistant Examiner* — Mark Luderer
(74) *Attorney, Agent, or Firm* — Birch, Stewart, Kolasch & Birch, LLP

(57) ABSTRACT

Provided is a compound which thickens or gels a fluid organic material to a desired viscosity, or which uniformly stabilizes the formulation of a composition containing the fluid organic material.
The compound according to the present invention is represented by Formula (1):

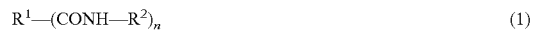

$$R^1-(CONH-R^2)_n \qquad (1)$$

where $R^1$ represents an n-valent aromatic hydrocarbon group containing two or more benzene rings; $R^2$ represents an aliphatic hydrocarbon group containing 6 or more carbon atoms; and n represents an integer of 4 or more. The group $R^1$ is preferably a group corresponding to an aromatic hydrocarbon selected from the group consisting of benzophenone, biphenyl, and naphthalene, except for removing hydrogen atoms in a number of n from the aromatic hydrocarbon. A thickening/stabilizing agent according to the present invention includes the compound.

5 Claims, No Drawings

(56) References Cited

OTHER PUBLICATIONS

International Search Report issued in PCT/JP2014/052534, mailed on Apr. 28, 2014.
Joester et al., "Amphiphilic Dendrimers with Heteroleptic Bis([2,2':6',2"]terpyridine)-Ruthenium(II) Cores", Helvetica Chimicaacta, vol. 87, 2004, pp. 2896-2918.
Lou et al., "Unusual Analyte-Matrix Adduct Ions and Mechanism of Their Formation in MALDI TOF MS of Benzene-1,3,5-Tricarboxamide and Urea Compounds", Journal of the American Society for Mass Spectrometry, vol. 24, Issue 9, 2013, pp. 1405-1412.
Sase et al., "Piezochromic luminescence of amide and ester derivatives of tetraphenylpyrene—role of amide hydrogen bonds in sensitive piezochromic response", Journal of Materials Chemistry, vol. 21, No. 23, 2011, pp. 8347-8354.

* cited by examiner

THICKENING STABILIZER, AND THICKENING/STABILIZING COMPOSITION USING THE SAME

TECHNICAL FIELD

The present invention relates to a novel compound having the action of thickening/stabilizing a fluid organic material such as an oil; a thickening/stabilizing agent including the compound; and a thickened/stabilized composition containing the agent. The present application claims priority to Japanese Patent Application No. 2013-022906 filed to Japan on Feb. 8, 2013, the entire contents of which are incorporated herein by reference.

BACKGROUND ART

Liquid thickening/stabilizing techniques are industrially very important. For example, thickening/stabilizing of aqueous components in metastable emulsions, such as mayonnaise and salad dressing, allows the metastable emulsions to maintain their emulsion states stably over a long time.

For the thickening/stabilizing, various thickening/stabilizing agents have been developed. Typically, hydrophilic thickening/stabilizing agents are compounds that thicken and/or stabilize aqueous media (aqueous vehicles) and known typically as alkyl acrylate copolymers.

In contrast, thickening/stabilizing agents for fluid organic materials are known typically as 12-hydroxystearic acid (e.g., Patent Literature (PTL) 1). The term "fluid organic material" refers to an organic material having fluidity, such as an oily medium. 12-hydroxystearic acid is utilized mainly in waste disposal of edible oils while using the gelling action thereof. However, 12-hydroxystearic acid fails to give a degree of gelation as adjusted, and can only induce the material into either one of a completely solidified state and a liquid state as intact. Specifically, there has not yet been found a compound that thickens and/or gels a fluid organic material to a desired viscosity.

CITATION LIST

Patent Literature

PTL 1: Japanese Unexamined Patent Application Publication (JP-A) No. H01-163111

SUMMARY OF INVENTION

Technical Problem

Accordingly, the present invention has an object to provide a compound that thickens and/or gels a fluid organic material to a desired viscosity, or uniformly stabilizes the formulation of a composition containing the fluid organic material.

The present invention has another object to provide a thickening/stabilizing agent containing the compound; a thickened/stabilized composition that is thickened, gelled, and/or stabilized by the thickening/stabilizing agent; and a method for producing the composition.

Solution to Problem

After intensive investigations to achieve the objects, the present inventors have found a compound having a specific structure and have found that the compound can thicken and/or gel a fluid organic material, and/or can uniformly stabilize the formulation of a composition containing the fluid organic material; and that the compound, when selectively used according to the type of the fluid organic material, can thicken and/or gel the fluid organic material to a desired viscosity, and/or can uniformly stabilize the formulation of a composition containing the fluid organic material. The present invention has been made based on these findings.

Specifically, the present invention provides a compound represented by Formula (1):

where $R^1$ represents an n-valent aromatic hydrocarbon group containing two or more benzene rings; $R^2$ represents an aliphatic hydrocarbon group containing 6 or more carbon atoms; and n represents an integer of 4 or more.

In the compound, $R^1$ in Formula (1) may be a group corresponding to an aromatic hydrocarbon selected from the group consisting of benzophenone, biphenyl, and naphthalene, except for removing hydrogen atoms in a number of n from the aromatic hydrocarbon.

The present invention also provides a thickening/stabilizing agent including the compound.

The present invention further provides a thickened/stabilized composition including the thickening/stabilizing agent and a fluid organic material.

In addition, the present invention provides a method for producing a thickened/stabilized composition. The method includes the step of dissolving the thickening/stabilizing agent and a fluid organic material in each other.

Specifically, the present invention relates to followings.

[1] A compound represented by Formula (1):

where $R^1$ represents an n-valent aromatic hydrocarbon group containing two or more benzene rings; $R^2$ represents an aliphatic hydrocarbon group containing 6 or more carbon atoms; and n represents an integer of 4 or more.

[2] The compound according to [1], in which $R^1$ in Formula (1) is a group corresponding to an aromatic hydrocarbon selected from the group consisting of benzophenone, biphenyl, and naphthalene, except for removing hydrogen atoms in a number of n from the aromatic hydrocarbon.

[3] A thickening/stabilizing agent including the compound according to one of [1] and [2].

[4] A thickened/stabilized composition including the thickening/stabilizing agent according to [3] and a fluid organic material.

[5] A method for producing a thickened/stabilized composition, the method including dissolving the thickening/stabilizing agent according to [3] and a fluid organic material in each other.

Advantageous Effects of Invention

The compound according to the present invention as represented by Formula (1), when dissolved in or blended with a fluid organic material, can easily thicken or gel the fluid organic material, or can uniformly stabilize the formulation of a composition containing the fluid organic material. The compound, when used typically in cosmetics, paints, foodstuffs, and pharmaceuticals, can adjust their viscosities within desired ranges, can maintain their formulations uniformly, and allow them to be used more satisfactorily.

DESCRIPTION OF EMBODIMENTS

Compound Represented by Formula (1)

The compound according to the present invention is represented by Formula (1):

$$R^1-(CONH-R^2)_n \qquad (1)$$

In Formula (1), $R^1$ represents an n-valent aromatic hydrocarbon group containing two or more benzene rings. $R^1$ is exemplified by a group corresponding to an aromatic hydrocarbon (preferably an aromatic hydrocarbon containing two benzene rings) selected typically from benzophenone, biphenyl, and naphthalene, except for removing hydrogen atoms in a number of n from the aromatic hydrocarbon.

In Formula (1), $R^2$ represents an aliphatic hydrocarbon group containing 6 or more carbon atoms. $R^2$ is exemplified by straight- or branched-chain alkyl groups containing about 6 to about 20 carbon atoms, such as hexyl, octyl, 2-ethylhexyl, decyl, dodecyl, tetradecyl, octadecyl, and nonadecyl groups, of which those containing 6 to 18 carbon atoms are preferred, and those containing 8 to 18 carbon atoms are particularly preferred; straight- or branched-chain alkenyl groups containing about 6 to about 20 carbon atoms, such as 2-hexenyl, 3-hexenyl, 4-hexenyl, 5-hexenyl, 7-octenyl, 9-decenyl, 11-dodecenyl, and 9-octadecenyl groups, of which those containing 6 to 18 carbon atoms are preferred, and those containing 12 to 18 carbon atoms are particularly preferred; and straight- or branched-chain alkynyl groups containing about 6 to about 20 carbon atoms, such as hexynyl, octynyl, decynyl, pentadecynyl, and octadecenyl groups, of which those containing 6 to 18 carbon atoms are preferred, and those containing 12 to 18 carbon atoms are particularly preferred.

In Formula (1), n represents an integer of 4 or more and is preferably 4 to 8, and particularly preferably 4 to 6.

Specifically, the compound represented by Formula (1) is exemplified by 3,3',4,4'-benzophenonetetracarboxylic acid tetra-($C_6$-$C_{20}$ alkyl or $C_6$-$C_{20}$ alkenyl)amides such as 3,3',4,4'-benzophenonetetracarboxylic acid tetrahexylamide, 3,3',4,4'-benzophenonetetracarboxylic acid tetraoctylamide, 3,3',4,4'-benzophenonetetracarboxylic acid tetradecylamide, 3,3',4,4'-benzophenonetetracarboxylic acid tetradodecylamide, 3,3',4,4'-benzophenonetetracarboxylic acid tetramyristylamide, 3,3',4,4'-benzophenonetetracarboxylic acid tetrastearylamide, and 3,3',4,4'-benzophenonetetracarboxylic acid tetraoleylamide; 1,1'-biphenyl-2,3,3',4'-tetracarboxylic acid tetra-($C_6$-$C_{20}$ alkyl or $C_6$-$C_{20}$ alkenyl)amides such as 1,1'-biphenyl-2,3,3',4'-tetracarboxylic acid tetrahexylamide, 1,1'-biphenyl-2,3,3',4'-tetracarboxylic acid tetraoctylamide, 1,1'-biphenyl-2,3,3',4'-tetracarboxylic acid tetradecylamide, 1,1'-biphenyl-2,3,3',4'-tetracarboxylic acid tetradodecylamide, 1,1'-biphenyl-2,3,3',4'-tetracarboxylic acid tetramyristylamide, 1,1'-biphenyl-2,3,3',4'-tetracarboxylic acid tetrastearylamide, and 1,1'-biphenyl-2,3,3',4'-tetracarboxylic acid tetraoleylamide; and 1,4,5,8-naphthalenetetracarboxylic acid tetra-($C_6$-$C_{20}$ alkyl or $C_6$-$C_{20}$ alkenyl)amides such as 1,4,5,8-naphthalenetetracarboxylic acid tetrahexylamide, 1,4,5,8-naphthalenetetracarboxylic acid tetraoctylamide, 1,4,5,8-naphthalenetetracarboxylic acid tetradecylamide, 1,4,5,8-naphthalenetetracarboxylic acid tetradodecylamide, 1,4,5,8-naphthalenetetracarboxylic acid tetramyristylamide, 1,4,5,8-naphthalenetetracarboxylic acid tetrastearylamide, and 1,4,5,8-naphthalenetetracarboxylic acid tetraoleylamide. Each of them may be used alone or in combination as the compound.

The compound represented by Formula (1) may be produced typically by a method (1) or a method (2) as follows.

In the method (1), an aromatic carboxylic acid [$R^1$—$(COOH)_n$ where $R^1$ and n are as with $R^1$ and n in Formula (1)] is allowed to react with thionyl chloride to give a carboxylic chloride, and the obtained carboxylic chloride is allowed to react with an aliphatic amine ($R^2$—$NH_2$ where $R^2$ is as with $R^2$ in Formula (1)). In the method (2), an aromatic carboxylic anhydride corresponding to the aromatic carboxylic acid is allowed to react with the aliphatic amine to give an amic acid, and the amic acid is further fused or condensed with the aliphatic amine using a carbodiimide. The method (1) is preferably employed in the present invention because the method allows a purification treatment to be easily performed upon production.

The aromatic carboxylic acid [$R^1$—$(COOH)_n$] is exemplified by a compound corresponding to an n-valent aromatic hydrocarbon group containing two or more benzene rings, except with four or more carboxy groups bonded thereto, such as 3,3',4,4'-benzophenonetetracarboxylic acid, 1,1'-biphenyl-2,3,3',4'-tetracarboxylic acid, and 1,4,5,8-naphthalenetetracarboxylic acid.

The aliphatic amine ($R^2$—$NH_2$) is exemplified by amines each containing an aliphatic hydrocarbon group containing 6 or more carbon atoms, such as hexylamine, octylamine, decylamine, dodecylamine, myristylamine, stearylamine, and oleylamine, of which those containing 6 to 20 carbon atoms are preferred. As the aliphatic hydrocarbon group, preferred is a straight- or branched-chain alkyl, alkenyl, or alkynyl group.

The reaction between the carboxylic chloride and the aliphatic amine in the method (1) may be performed typically by adding the carboxylic chloride dropwise to a system containing the aliphatic amine.

The reaction between the carboxylic chloride and the aliphatic amine may be performed in the presence of, or in the absence of, a solvent. The solvent is exemplified by saturated or unsaturated hydrocarbon solvents such as pentane, hexane, heptane, octane, and petroleum ether; aromatic hydrocarbon solvents such as benzene, toluene, and xylenes; halogenated hydrocarbon solvents such as methylene chloride, chloroform, 1,2-dichloroethane, chlorobenzene, and bromobenzene; ether solvents such as diethyl ether, diisopropyl ether, dibutyl ether, tetrahydrofuran, dioxane, 1,2-dimethoxyethane, and cyclopentyl methyl ether; nitrile solvents such as acetonitrile and benzonitrile; sulfoxide solvents such as dimethyl sulfoxide; sulfolane solvents such as sulfolane; amide solvents such as dimethylformamide; and high-boiling solvents such as silicone oils. Each of them may be used alone or in combination. Among them, any of halogenated hydrocarbon solvents is preferably used in the present invention because the reaction components (the carboxylic chloride and the aliphatic amine) are highly satisfactorily soluble in these solvents.

The solvent may be used in an amount of typically about 50 to about 300 percent by weight, and preferably 100 to 250 percent by weight, relative to the total amount of the carboxylic chloride and the aliphatic amine. The solvent, if used in an amount greater than the range, causes relatively lower concentrations of the reaction components, and this may readily cause a lower reaction rate.

The reaction (i.e., dropwise addition) of the carboxylic chloride with the aliphatic amine is generally performed at normal atmospheric pressure. The reaction may be performed in any atmosphere (i.e., atmosphere upon dropwise addition) not critical, as long as not adversely affecting the reaction. The atmosphere may be any atmosphere such as air atmosphere, nitrogen atmosphere, or argon atmosphere. The reaction may be performed at a temperature (i.e., temperature upon dropwise addition) of typically about 30° C. to about 60° C. The reaction may be performed for a time (i.e., dropwise addition time) of typically about 0.5 to about 20 hours. The method may further include an aging process after the completion of the reaction (i.e., dropwise addition). When the method includes the aging process, the aging may be performed at a temperature of typically about 30° C. to about 60° C. for a time of typically about 1 to about 5 hours. The reaction may be performed by any system such as batch system, semi-batch system, or continuous system.

After the completion of the reaction, the resulting reaction product can be separated/purified by a separation method such as filtration, concentration, distillation, extraction, crystallization, adsorption, recrystallization, or column chromatography, or a separation method as any combination of them.

The compound represented by Formula (1) undergoes self-association by the action of hydrogen bond at the amide bonding site to form a fibrous self-assembled structure. In addition, the compound includes a side chain ($R^2$ in Formula (1)) having affinity for a fluid organic material and, when dissolved mutually in or blended with a fluid organic material, can thicken and/or gel the fluid organic material, or can uniformly stabilize the formulation of a composition containing the fluid organic material. The compound is therefore useful as thickening/stabilizing agents, and, more specifically, useful as thickening agents, gelling agents, and/or stabilizing agents.

Thickening/Stabilizing Agent

The thickening/stabilizing agent (thickener/stabilizer) according to the present invention includes each of the compounds represented by Formula (1) alone or in combination.

As used herein the term "thickening/stabilizing agent" refers to a compound that is dissolved in a fluid organic material to develop viscosity. The concept "thickening/stabilizing agent" includes a thickening agent, a gelling agent, and a stabilizing agent, where the thickening agent imparts viscosity to the fluid organic material; the gelling agent gels the fluid organic material; and the stabilizing agent allows a composition containing the fluid organic material to have higher viscosity in order to uniformly stabilize the formulation of the composition.

The thickening/stabilizing agent according to the present invention may further include any of additional components as needed in addition to the compound(s) represented by Formula (1). The additional components are exemplified by bases (base ingredients), hydroxyfatty acids, acrylic polymers, oligomer esters (such as dextrin fatty acid esters), and particles typically of metal oxides. The thickening/stabilizing agent may contain the additional component(s) in a content within such a range that the content of the compound(s) represented by Formula (1) is typically 0.5 percent by weight or more, and preferably 1 percent by weight or more, based on the total amount (100 percent by weight) of the thickening/stabilizing agent. When the thickening/stabilizing agent includes two or more different compounds represented by Formula (1), the "content of the compound(s)" refers to the total content of the two or more compounds. The upper limit of the content of the compound(s) represented by Formula (1) is 100 percent by weight. The thickening/stabilizing agent, if containing the compound(s) represented by Formula (1) in a content out of the range, may tend to hardly thicken and/or gel a fluid organic material, or to hardly uniformly stabilize the formulation of a composition containing the fluid organic material.

The thickening/stabilizing agent according to the present invention can be in a form as selected from various forms such as powdery form, granular form, liquid form, and milky lotion form.

The thickening/stabilizing agent according to the present invention, when dissolved mutually in or blended with a fluid organic material, can thicken and/or gel the fluid organic material, where the thickening and/or gelling can be performed so as to allow the fluid organic material to have a desired viscosity according to an intended purpose within the range of greater than about 1 time to about 600 times the original viscosity of the fluid organic material. The dissolving/blending is preferably performed by mixing and heating the components to dissolve them in or to blend them with each other, and then cooling the resulting blend.

Thickened/Stabilized Composition

The thickened/stabilized composition according to the present invention is a composition including the thickening/stabilizing agent and a fluid organic material, in which the fluid organic material is thickened and/or gelled by the thickening/stabilizing agent, and/or the formulation of the composition containing the fluid organic material is uniformly stabilized.

The fluid organic material may be an organic material having a viscosity of less than 0.1 Pa·s, where the viscosity is measured as a viscosity ($\eta$) at 25° C. and a shear rate of 10 (1/s)] with a rheometer. The fluid organic material is exemplified by hydrocarbon oils such as hexane, cyclohexane, isododecane, benzene, toluene, poly-alpha-olefins, and liquid paraffin; ethers such as tetrahydrofuran; halogenated hydrocarbons such as carbon tetrachloride and chlorobenzene; petroleum components such as kerosene (paraffin oil), gasoline (petrol), light oil, and heavy oil; animal and vegetable oils such as sunflower oil, olive oil, soybean oil, corn oil, castor oil, beef tallow, jojoba oil, and squalane; silicones such as dimethylpolysiloxanes and methylphenylpolysiloxanes; esters such as octyldodecyl oleate, cetyl ethylhexanoate, glyceryl triisooctanoate, and neopentyl glycol diisooctanoate; aromatic carboxylic acids; and pyridine. Each of them may be used alone or in combination as the fluid organic material.

The thickened/stabilized composition according to the present invention may further contain any of additional components within ranges not adversely affecting advantageous effects of the present invention, in addition to the thickening/stabilizing agent and the fluid organic material. Such additional components are exemplified by medicinal components, pigments, flavors, and other compounds to be contained, in addition to the fluid organic material, in compositions desiring to be thickened/stabilized. The compositions are exemplified by compositions of cosmetics, paints, foodstuffs, and pharmaceuticals.

The thickened/stabilized composition may be produced through the step of dissolving or blending the thickening/stabilizing agent and the fluid organic material in each other. More specifically, the thickened/stabilized composition may be produced by mixing the whole quantities of the thickening/stabilizing agent and the fluid organic material, heating them to be dissolved in or blended with each other, and cooling the resulting blend. Alternatively, the thickened/stabilized composition may be produced by mixing the thickening/stabilizing agent with part of the fluid organic material, heating them to be dissolved in or blended with each other, cooling the resulting blend to give a thickened/stabilized composition, and mixing the composition with the remainder of the fluid organic material.

The thickening/stabilizing agent may be used (mixed) in an amount of typically 0.1 to 100 parts by weight, preferably 0.5 to 90 parts by weight, and particularly preferably 1 to 80 parts by weight, per 1000 parts by weight of the fluid organic material, while the amount may vary depending on the type of the fluid organic material. The thickening/stabilizing agent, when mixed (used) in an amount within the range, can give a composition in which the fluid organic material is thickened and/or gelled, or can give a composition whose formulation is uniformly stabilized.

The temperature upon heating may be selected as appropriate according to the types of the thickening/stabilizing agent and the fluid organic material to be used, is not critical, as long as being a temperature at which the thickening/stabilizing agent and the fluid organic material are dissolved in or blended with each other. However, the heating temperature is preferably not higher than 100° C. and, when the fluid organic material has a boiling point of 100° C. or lower, is preferably around the boiling point.

It is enough that the cooling after dissolving/blending is performed so as to cool the resulting mixture to 25° C. or lower. The cooling may be performed as slow cooling at room temperature or as forced cooling typically with ice.

The thickened/stabilized composition according to the present invention can have a viscosity as adjusted as appropriate within the range from greater than 1 time to 600 times the viscosity of the fluid organic material contained in the composition, where the viscosity is measured with a rheometer as a viscosity ($\eta$) at 25° C. and a shear rate of 10 (1/s).

The thickened/stabilized composition according to the present invention is not limited, as long as being a composition desiring to be thickened/stabilized, and is exemplified by compositions of cosmetics, paints, foodstuffs, and pharmaceuticals.

EXAMPLES

The present invention will be illustrated in further detail with reference to several examples below. It should be noted, however, that the examples are by no means intended to limit the scope of the present invention.

Synthesis Example 1

Synthesis of thickening/stabilizing agent
(BTDA-$C_6$: 3,3',4,4'-benzophenonetetracarboxylic acid tetrahexylamide)

In a 100-mL four-neck separable flask equipped with a Dimroth condenser, a nitrogen inlet, a dropping funnel, and a thermocouple, 20 mL of $CHCl_3$ and 11.41 g (0.113 mol) of hexylamine were placed. While setting the system internal temperature to 50° C., 6.59 g (0.141 mol) of 3,3',4,4'-benzophenonetetracarboxy-tetrachloride (hereinafter also referred to as "BTDA-Cl") was added dropwise over 2.5 hours, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (70/30 (v/v)) and yielded 5.0 g of BTDA-$C_6$ in a yield of 42%.

$^1$H-NMR (270 MHz, $CDCl_3$): $\delta$ 0.91 (t, 12H, J=4.9 Hz), 1.35-1.45 (m, 24H), 1.57-1.72 (m, 8H), 3.38 (q, 8H, J=6.8 Hz), 7.45-7.54 (m, 4H), 7.65-7.73 (m, 6H)

Synthesis Example 2

Synthesis of Thickening/Stabilizing Agent
(BTDA-$C_8$: 3,3',4,4'-benzophenonetetracarboxylic acid tetraoctylamide)

In a 100-mL four-neck separable flask equipped with a Dimroth condenser, a nitrogen inlet, a dropping funnel, and a thermocouple, 20 mL of $CHCl_3$ and 13.77 g (0.106 mol) of n-octylamine were placed. While setting the system internal temperature to 40° C., 6.23 g (0.133 mol) of "BTDA-Cl" was added dropwise over 2.5 hours, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (70/30 (v/v)) and yielded 5.4 g of BTDA-$C_8$ in a yield of 43%.

$^1$H-NMR (270 MHz, $CDCl_3$): $\delta$ 0.88 (t, 12H, J=6.2 Hz), 1.18-1.40 (m, 40H), 1.59-1.61 (m, 8H), 3.35-3.42 (m, 8H), 7.28-7.53 (m, 4H), 7.69-8.14 (m, 6H)

Synthesis Example 3

Synthesis of thickening/stabilizing agent
(BTDA-$C_{12}$: 3,3',4,4'-benzophenonetetracarboxylic acid tetradodecylamide)

In a 100-mL four-neck separable flask equipped with a Dimroth condenser, a nitrogen inlet, a dropping funnel, and a thermocouple, 20 mL of $CHCl_3$ and 11.4 g (0.062 mol) of dodecylamine were placed. While setting the system internal temperature to 50° C., 4.97 g (0.011 mol) of "BTDA-Cl" was added dropwise over 0.5 hour, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (70/30 (v/v)) and yielded 2.4 g of BTDA-$C_{12}$ in a yield of 27%.

$^1$H-NMR (270 MHz, $CDCl_3$): $\delta$ 0.88 (t, 12H, J=7.3 Hz), 1.05-1.44 (m, 72H), 1.59-1.61 (m, 8H), 3.38 (m, 8H), 7.34-7.52 (m, 2H), 7.67-7.70 (m, 2H), 7.77 (s, 2H)

Synthesis Example 4

Synthesis of Thickening/Stabilizing Agent
(BTDA-$C_{14}$: 3,3',4,4'-benzophenonetetracarboxylic acid tetramyristylamide)

In a 100-mL four-neck separable flask equipped with a Dimroth condenser, a nitrogen inlet, a dropping funnel, and a thermocouple, 20 mL of $CHCl_3$ and 13.2 g (0.062 mol) of myristylamine were placed. While setting the system internal temperature to 50° C., 4.97 g (0.011 mol) of "BTDA-Cl" was added dropwise over 0.5 hour, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (70/30 (v/v)) and yielded 3.1 g of BTDA-$C_{14}$ in a yield of 31%.

$^1$H-NMR (270 MHz, $CDCl_3$): $\delta$ 0.88 (t, 12H, J=6.8 Hz), 1.12-1.41 (m, 88H), 1.45-1.65 (m, 8H), 3.38 (dd, 8H, J=13.2 Hz, 6.5 Hz), 7.26-7.68 (m, 6H), 7.69-7.72 (m, 2H), 7.79 (s, 2H)

Synthesis Example 5

Synthesis of Thickening/Stabilizing Agent
(BTDA-$C_{18}$: 3,3',4,4'-benzophenonetetracarboxylic acid tetrastearylamide)

In a 100-mL four-neck separable flask equipped with a Dimroth condenser, a nitrogen inlet, a dropping funnel, and a thermocouple, 20 mL of $CHCl_3$ and 24.65 g (0.091 mol) of stearylamine were placed. While setting the system internal temperature to 50° C., 5.35 g (0.011 mol) of "BTDA-Cl" was added dropwise over 2.5 hours, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (80/20 (v/v)) and yielded 5.4 g of BTDA-$C_{18}$ in a yield of 31%.

$^1$H-NMR (270 MHz, $CDCl_3$): δ 0.88 (t, 12H, J=6.8 Hz), 1.12-1.41 (m, 120H), 1.45-1.65 (m, 8H), 3.35-3.40 (m, 8H), 7.37-7.58 (m, 6H), 7.65-7.81 (m, 4H)

Synthesis Example 6

Synthesis of Thickening/Stabilizing Agent
(BTDA-oleyl: 3,3',4,4'-benzophenonetetracarboxylic acid tetraoleylamide)

In a 100-mL four-neck separable flask equipped with a Dimroth condenser, a nitrogen inlet, a dropping funnel, and a thermocouple, 20 mL of $CHCl_3$ and 12.31 g (0.046 mol) of oleylamine were placed. While setting the system internal temperature to 50° C., 2.69 g (0.0058 mol) of "BTDA-Cl" was added dropwise over 2.5 hours, followed by aging for further 4 hours to give a crude mixture. The crude mixture, after the removal of a low-boiling component on an evaporator, was washed with methanol and yielded a pale yellow wet powder. The resulting wet powder was recrystallized from $CHCl_3/CH_3OH$ (70/30 (v/v)) and yielded 3.4 g of BTDA-oleyl in a yield of 39%.

$^1$H-NMR (270 MHz, $CDCl_3$): δ 0.84-0.87 (m, 12H), 1.06-1.41 (m, 88H), 1.42-1.57 (m, 8H), 1.75-2.11 (m, 16H), 3.21-3.48 (m, 8H), 5.31-5.52 (m, 8H), 7.43-8.10 (m, 10H)

Examples 1 to 6

An aliquot (1 cm$^3$) of each of a variety of fluid organic materials indicated in Table 1 was weighed in a test tube and combined and mixed with 10 mg of each of the thickening/stabilizing agents prepared in Synthesis Examples 1 to 6. The resulting mixtures were heated and stirred at appropriate temperatures for individual fluid organic materials so as to dissolve or blend the fluid organic material and the thickening/stabilizing agent in each other and yielded a series of thickened/stabilized compositions. The appropriate temperatures were as follows. For a fluid organic material having a boiling point lower than 100° C., the temperature was a temperature (40° C. to 80° C.) equal to or lower than the boiling point; whereas, for a fluid organic material having a boiling point of 100° C. or higher, the temperature was 80° C. to 100° C. Specifically, the temperature were: 40° C. for hexane; 40° C. for cyclohexane; 100° C. for sunflower oil; 80° C. for isododecane; 80° C. for liquid paraffin; 80° C. for cetyl ethylhexanoate; and 80° C. for poly-alpha-olefin, each used as the fluid organic material.

The resulting thickened/stabilized compositions were cooled down to 25° C., and the viscosities thereof were measured. To which times the viscosity of each fluid organic material was thickened (increased) was determined, and the thickening stability was evaluated according to following criteria.

Criteria
1: from greater than 1.0 time to 2.0 times;
2: from greater than 2.0 times to 4.8 times;
3: from greater than 4.8 times to 10 times;
4: from greater than 10 times to 50 times;
5: from greater than 50 times to 100 times; and
6: from greater than 100 times to 600 times.

The viscosities of the fluid organic materials and the thickened/stabilized compositions were measured and determined each in the following manner. The measurement was performed using a viscosity/visco-elastometer (rheometer) (HAAKE RheoStress 600 (trade name)) equipped with a cone-and-plate sensor and a Peltier temperature controller. The sensor used had a diameter of 60 mm with a cone angle of 1°, or a diameter of 35 mm with a cone angle of 1°, 2°, or 4°. The viscosities were measured in a steady flow viscosity measurement mode at 25° C. and at different shear rates varying in a log scale from 0.001 to 100 (1/s), based on which a viscosity curve was plotted. A viscosity at a shear rate of 10 (1/s) was determined from the viscosity curve, and this was defined as the viscosity in the present invention. Each plot employed values obtained when the torque value variation of the instrument was settled within the range of 5% and the data became stable.

The results are summarized in the following table.

TABLE 1

| | | Example 1 BTDA-$C_6$ | Example 2 BTDA-$C_8$ | Example 3 BTDA-$C_{12}$ | Example 4 BTDA-$C_{14}$ | Example 5 BTDA-$C_{18}$ | Example 6 BTDA-oleyl |
|---|---|---|---|---|---|---|---|
| Fluid organic material | Hexane | 1 | 5 | 1 | 1 | 1 | 5 |
| | Cyclohexane | 1 | 5 | 1 | 1 | 1 | 5 |
| | Sunflower oil | 3 | 1 | 1 | 1 | 2 | 2 |
| | Isododecane | 4 | 6 | 6 | 5 | 6 | 1 |
| | Liquid paraffin | 1 | 1 | 1 | 1 | 2 | 2 |
| | Cetyl ethylhexanoate | 2 | 2 | 2 | 2 | 4 | 3 |
| | Poly-alpha-olefin | 1 | 2 | 3 | 5 | 4 | 2 |

INDUSTRIAL APPLICABILITY

The compound according to the present invention as represented by Formula (1), when dissolved mutually in or blended with a fluid organic material, can easily thicken and/or gel the fluid organic material, or can uniformly stabilize the formulation of a composition containing the fluid organic material. The compound, when used typically in cosmetics, paints, foodstuffs, and pharmaceuticals, can therefore adjust their viscosities within desired ranges, can uniformly maintain their formulations, and allow them to be used more satisfactorily.

The invention claimed is:

1. A compound of Formula (1):

$$R^1\text{—}(CONH\text{—}R^2)_n \qquad (1)$$

wherein $R^1$ group is an n-valent aromatic hydrocarbon group selected from the group consisting of benzophenone, biphenyl, and naphthalene, except for removing hydrogen atoms in a number of n from the aromatic hydrocarbon group; $R^2$ groups are independently an aliphatic hydrocarbon group comprising 6 or more carbon atoms; and n represents an integer of 4 or more.

2. A thickening/stabilizing agent comprising the compound according to claim 1.

3. A thickened/stabilized composition comprising:
the thickening/stabilizing agent according to claim 2; and
a fluid organic material.

4. A method for producing a thickened/stabilized composition, the method comprising the step of:
dissolving the thickening/stabilizing agent according to claim 2 and a fluid organic material in each other.

5. The compound of claim 1, wherein at least one aliphatic hydrocarbon group $R^2$ is selected from the group consisting of straight- or branched-chain alkyl group containing 8 to 18 carbon atoms, straight- or branched-chain alkenyl group containing 12 to 18 carbons and straight- or branched-chain alkynyl group containing 12 to 18 carbon atoms.

* * * * *